United States Patent
Erkens et al.

(10) Patent No.: US 11,077,038 B2
(45) Date of Patent: Aug. 3, 2021

(54) COSMETIC SHAMPOOS WITH LOW WATER CONTENT IN A POUCH

(71) Applicant: Henkel AG & Co. KGaA, Duesseldorf (DE)

(72) Inventors: Udo Erkens, Willich (DE); Torsten Lechner, Langenfeld (DE); Thomas Schroeder, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 108 days.

(21) Appl. No.: 16/162,738

(22) Filed: Oct. 17, 2018

(65) Prior Publication Data
US 2019/0110970 A1   Apr. 18, 2019

(30) Foreign Application Priority Data
Oct. 18, 2017   (DE) .......... 10 2017 218 599

(51) Int. Cl.
| | | |
|---|---|---|
| *A61K 8/00* | (2006.01) | |
| *A61K 8/41* | (2006.01) | |
| *A61K 8/81* | (2006.01) | |
| *A61K 8/37* | (2006.01) | |
| *A61K 8/46* | (2006.01) | |
| *A61K 8/02* | (2006.01) | |
| *A61K 8/34* | (2006.01) | |
| *A61K 8/86* | (2006.01) | |
| *A61Q 5/02* | (2006.01) | |
| *B65D 65/46* | (2006.01) | |

(52) U.S. Cl.
CPC ............ *A61K 8/416* (2013.01); *A61K 8/0204* (2013.01); *A61K 8/342* (2013.01); *A61K 8/345* (2013.01); *A61K 8/37* (2013.01); *A61K 8/375* (2013.01); *A61K 8/463* (2013.01); *A61K 8/8135* (2013.01); *A61K 8/86* (2013.01); *A61Q 5/02* (2013.01); *B65D 65/46* (2013.01); *A61K 2800/5424* (2013.01); *A61K 2800/5426* (2013.01); *A61K 2800/596* (2013.01); *A61K 2800/87* (2013.01)

(58) Field of Classification Search
None
See application file for complete search history.

(56) References Cited

U.S. PATENT DOCUMENTS

| | | | | |
|---|---|---|---|---|
| 6,710,022 B1 * | 3/2004 | Kwetkat | ................. | A61K 8/04 510/119 |
| 8,276,756 B2 * | 10/2012 | Denome | .................... | C08J 5/18 206/524.7 |
| 2004/0152610 A1 * | 8/2004 | Engel | ..................... | A45D 37/00 510/296 |
| 2016/0045417 A1 * | 2/2016 | Schroeder | ................ | A61Q 5/02 132/202 |
| 2017/0298216 A1 * | 10/2017 | Labeque | .................. | B65B 1/02 |

FOREIGN PATENT DOCUMENTS

| | | | |
|---|---|---|---|
| CN | 105662929 A | * | 6/2016 |
| GB | 2382350 A | | 5/2003 |
| WO | 2016000128 A1 | | 1/2016 |
| WO | 2016061069 A2 | | 4/2016 |
| WO | 2016179096 A1 | | 11/2016 |
| WO | 2018081494 A2 | | 5/2018 |

* cited by examiner

*Primary Examiner* — Susan T Tran
(74) *Attorney, Agent, or Firm* — Lorenz & Kopf, LLP

(57) ABSTRACT

The present disclosure relates to a cosmetic product cleaning and care of the keratinous, fibres, in particular human hair, comprising
(i) a pouch, comprising at least one sealed chamber, wherein the sealed chamber has at least one wall made from a water-soluble foil, and
(ii) a shampoo composition, which is present in the sealed chamber of the pouch, wherein the shampoo composition contains—relative to its total weight
(iia) from about 0 to about 20 wt % water
(iib) at least one anionic tenside and
(iic) at least one cationic tenside.

4 Claims, No Drawings

COSMETIC SHAMPOOS WITH LOW WATER CONTENT IN A POUCH

CROSS-REFERENCE TO RELATED APPLICATION

This application claims priority to German Patent Application No. 10 2017 218 599.6, filed Oct. 18, 2017, which is incorporated herein by reference in its entirety.

TECHNICAL FIELD

The present disclosure relates to a cosmetic product for cleaning and caring for keratinous fibres, in particular human hair, comprising a pouch with at least one chamber, wherein the pouch (i.e. the chamber of the pouch) is made from a water-soluble foil. A shampoo composition constituted with little or no water and containing at least one anionic tenside and at least one cationic tenside is packed in this at least one chamber.

BACKGROUND

Water-soluble polymer foils are known as packaging materials in the related art. For example, measured amounts of liquid detergents or washing-up liquids may be made available to the user in prepared form for one-time use in such foil packaging. The user can place the pouch, pouches or sachets directly in the washing machine or dishwasher. The foil dissolves during use, releasing its contents.

This form of measured release offers the user various advantages. The risk of using too much of the active ingredient is avoided, and if the foil is dissolved completely the user does not have to dispose of the packaging separately. Thus, this form of measured dosing and application is particularly convenient for the user.

WO 2016/061069 A2 describes pouches containing liquid cleaning agents. In principle, this document also discloses their constitution in the form of a shampoo, but the previously known application forms are still associated with various drawbacks.

Single use in the form of a pouch in the cosmetics branch places a number of quite particular requirements on the formulations present in the pouch, particularly if they are care shampoos.

In order to offer a sufficiently high cleaning performance, a care shampoo must contain a significant quantity of one or more anionic detergent tensides. If at the same time a care effect is to be achieved, the shampoo also contains at least one ingredient with treatment or conditioning action. Treatment or conditioning substances used may be cationic tensides for example.

Even in aqueous solution, the use of anionic and cationic tensides together presents challenges for the person skilled in the art, because particularly if they are incompatible or are used in excessive quantities the anionic and cationic tensides neutralise each other and are then precipitated out of the aqueous solution as an inorganic ion pair.

The wall of the pouch is made from a water-soluble foil. In order to prevent it from dissolving prematurely, the water content of the formulation in the pouch must therefore be as low as possible.

The constitution of anionic tensides and cationic tensides together in a shampoo formulation containing little or no water presents a correspondingly greater risk that the two ionic compounds will not be sufficiently solvated, and will be precipitated from the formulation.

BRIEF SUMMARY

Cosmetic product for cleaning and care of keratinous fibres, comprising
(i) a pouch, comprising at least one sealed chamber, wherein the sealed chamber has at least one wall made from a water-soluble foil, and
(ii) a shampoo composition, which is present in the sealed chamber of the pouch, wherein the shampoo composition comprises—relative to its total weight
(iia) from about 0 to about 20 wt % water
(iib) at least one anionic tenside and
(iic) at least one cationic tenside.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was therefore to provide a cosmetic product which may be used in the form of a pouch, and which has both a cleaning and care effect. The product should be aesthetically attractive, no undesirable solids should form in the shampoo composition, and it should have good long-term storage stability.

Surprisingly, it has now been found that cleaning cosmetic shampoos in the form or a pouch can be prepared if water-soluble foil is used to manufacture the pouch and if the shampoos include a certain content of water and anionic and cationic tensides.

A first object of the present disclosure is a cosmetic product for cleaning and care of keratinous fibres, in particular human hair, comprising
(i) a pouch, comprising at least one sealed chamber, wherein the sealed chamber has at least one wall made from a water-soluble foil, and
(ii) a shampoo composition, which is present in the sealed chamber of the pouch, wherein the shampoo composition contains—relative to its total weight
(iia) from about 0 to about 20 wt % water
(iib) at least one anionic tenside and
(iic) at least one cationic tenside.

Keratinous Fibres

The product as contemplated herein is a product for cleaning and care of keratinous fibres, in particular human hair. The term keratinous fibres is understood to include wool, fur, feathers, and in particular human hair.

Pouch

The cosmetic product as contemplated herein comprises at least one pouch, which in turn comprises at least one sealed chamber. The chamber(s) have at least one wall which includes a water-soluble foil.

In other words, the pouch is preferably manufactured from a water-soluble foil and forms at least one chamber, wherein the chamber is sealed and locked or closed off The shampoo composition as contemplated herein is packed in the water-soluble foil and in this state is located in the sealed chamber of the pouch.

Thus, expressed differently the first object of the present disclosure is a cosmetic product for cleaning and caring for keratinous fibres, in particular human hair, comprising (i) a pouch, comprising at least one sealed chamber made of a water-soluble foil, and
(ii) a shampoo composition contained inside the sealed chamber of the pouch, wherein the shampoo composition contains—relative to its total weight
(iia) from about 0 to about 20 wt % water
(iib) at least one anionic tenside and
(iic) at least one cationic tenside.

Thus, expressed differently the first object of the present disclosure is a cosmetic product for cleaning and caring for keratinous fibres, in particular human hair, comprising
(i) a pouch comprising at least one sealed chamber, wherein the sealed chamber includes a water-soluble foil, and
(ii) a shampoo composition contained inside the sealed chamber of the pouch, wherein the shampoo composition contains—relative to its total weight
(iia) from about 0 to about 20 wt % water
(iib) at least one anionic tenside and
(iic) at least one cationic tenside.

In this context, the pouch may comprise only one chamber. The situation in which the pouch also comprises multiple chambers also falls within the scope of the present disclosure. If the pouch comprises multiple chambers, said chambers preferably contain formulations of different composition.

The preparations of different composition are then present in the water-soluble foil, but packed separately. i.e. in a two-chamber pouch in which the two preparations are packed separately from one another but the chambers are connected to each other by foil, or the chambers have foil functioning as a partition wall between them.

The pouch particularly preferably has exactly one sealed chamber.

Water-Soluble Foil

A substance that is often used for manufacturing water-soluble foils is polyvinyl alcohol (PVOH). Polyvinyl alcohol is a thermoplastic which is most often produced by saponification (hydrolysis) of polyvinyl acetate (PVAC). The direct synthesis path (i.e. polycondensation of vinyl alcohol) is not possible. Polyvinyl alcohol is resistant to practically all anhydrous organic solvents.

In a preferred embodiment, the product as contemplated herein therefore comprises a pouch, wherein the pouch (or the sealed chamber of the pouch) is manufactured from a water-soluble foil that contains a polyvinyl alcohol polymer, a polyvinyl alcohol copolymer, or also a mixture of several polyvinyl alcohol polymers and/or polyinvyl alcohol copolymers.

In a particularly preferred embodiment, a product as contemplated herein is exemplified in that
(ia) the water-soluble foil comprises one or more polyvinyl alcohol polymers (PVOH polymers) and/or polyvinyl alcohol copolymers (PVOH copolymers).

In the manufacture of polyvinyl alcohol from polyvinyl acetate, the acetyl groups can be split off by either acid or alkaline hydrolysis.

Fully hydrolysed polyvinyl alcohol—in which all acetyl groups have been converted into hydroxy groups—is a highly crystalline polymer in which strong hydrogen bridge bonds are formed. Fully hydrolysed polyvinyl alcohol has high mechanical stability, but only dissolves in hot water.

If a certain quantity of acetyl groups remains unchanged in the polymer of the polyvinyl acetate, a copolymer of the polyvinyl alcohol is created which is also described as partially saponified or partially hydrolysed. Since the hydrolysis is only partial, the number of hydrogen bridges is reduced and the crystallinity is diminished, and the polymer can also be dissolved in cold water. Partially saponified polyvinyl alcohol (PVOH) types containing about from about 10 to about 20 wt % polyvinyl acetate (PVAC) dissolve particularly readily in water.

The degree of hydrolysis of the polyvinyl alcohol may be for example at values from about 75% to about 99%. In this context, the percentages mean that about 75% of the vinyl acetate units have been hydrolysed and converted to the corresponding hydroxy groups. The degree of hydrolysis is preferably from about 79 to about 92%, the degree of hydrolysis is most particularly in the range from about 90 to about 99%.

The degree of hydrolysis (or also degree of deacetylation) may be determined for example by measuring the polymer using quantitative $^1$H-NMR and/or $^{13}$C-NMR spectroscopy and comparing it with a fully acetylated or deacetylated reference polymer or other suitable standard.

The manufacture of the water-soluble foil preferably involves the use of polyvinyl alcohol polymers (PVOH polymers) and/or polyvinyl alcohol copolymers (PVOH copolymers). Although the aforementioned polymers can be processed in a blend with yet further polymers to create the foil, it is still particularly preferred if the PVOH polymer and/or the PVOH copolymer are used as the main components of the foil. This, it is particularly preferred if at least about 50 wt %, preferably at least about 60 wt %, more preferably at least about 70 wt %, and most particularly preferably at least about 85 wt % of the water-soluble foil includes one or more polyvinyl alcohol polymers (PVOH polymer) and/or polyvinyl alcohol copolymers (PVOH copolymer) relative to its total weight.

In other words, the minimum quantity of all PVOH polymers and PVOH copolymers used to manufacture the foil is preferably at least about 50 wt %. In this context, the unit of quantity wt % is used, referring to the total weight of the foil.

In a particularly preferred embodiment, a product as contemplated herein is exemplified in that
(ia) at least about 50 wt %, preferably at least about 60 wt %, more preferably at least about 70 wt %, and most particularly preferably at least about 85 wt % of the water-soluble foil includes one or more polyvinyl alcohol polymers (PVOH polymer) and/or polyvinyl alcohol copolymers (PVOH copolymer) relative to its total weight.

For the purposes of the present disclosure, the term polyvinyl alcohol polymer (PVOH polymer) is understood to refer to the homopolymer of polyvinyl alcohol, i.e, formally the polymer is constructed exclusively of repeat units of the vinyl alcohol.

A copolymer is a polymer that contains structurally different monomer units (or also repeat units). A copolymer is composed of at least two structurally different repeat units.

A polyvinyl alcohol copolymer (PVOH copolymer) as contemplated herein with two different monomer units is for example a polymer which contains repeat units proceeding from vinyl alcohol and vinyl acetate. Thus, the partially hydrolysed polyvinyl alcohol polymer described earlier is a polyvinyl alcohol copolymer (PVOH copolymer) as contemplated herein, and in the following text it will be referred to as polyvinyl alcohol/polyvinyl acetate copolymer A particularly preferred product is therefore exemplified in that
(ia) the water-soluble foil comprises one or more polyvinyl alcohol/polyvinyl acetate copolymers.

Besides vinyl acetate, a copolymer of polyvinyl alcohol may further contain a third, structurally different monomer unit (or repeat unit). Suitable polyvinyl alcohol copolymers in this category might be for example
copolymers of vinyl alcohol, vinyl acetate and maleic acid
copolymers of vinyl alcohol, vinyl acetate and maleic acid ester
copolymers of vinyl alcohol, vinyl acetate and fumaric acid
copolymers of vinyl alcohol, vinyl acetate and itaconic acid
copolymers of vinyl alcohol, vinyl acetate and vinylsulfonic acid
copolymers of vinyl alcohol, vinyl acetate and 2-acrylamido-1-methylpropane sulfonic acid
copolymers of vinyl alcohol, vinyl acetate and 2-acrylamido-2-methylpropane sulfonic acid
copolymers of vinyl alcohol, vinyl acetate and acrylamide
copolymers of vinyl alcohol, vinyl acetate and (meth)acrylic acid
copolymers of vinyl alcohol, vinyl acetate and (meth)acrylic acid ester A polyvinyl alcohol polymer or polyvinyl alcohol copolymer may be used to produce the water-soluble foil. However, it is also possible to use different polymers to produce the foil. The mixture of the different polymers is also referred to as a "blend" in this context.

Foils made from polymer-Blends, i.e. foils which contain several different polymers, may offer significant advantages in terms of water-solubility and the application properties.

For example, a blend (i.e. a polymer mixture) of various polyvinyl alcohol/polyvinyl acetate copolymers having different viscosities may be used to produce the water-soluble foil. In this context the viscosity of the polymer is understood to refer to the viscosity of a standardised solution of the polymer.

The following method for determining viscosity is recognised internationally: The polyvinyl alcohol/polyvinyl acetate copolymer is dissolved in water at 20° C., creating a 4% solution. All viscosities are expressed in cP and refer to the viscosity of the 4% solution (specified in wt %) in water at a temperature of 20° C. Measurement is carried out in a Brookfield LV viscosimeter with a UL adapter. Regarding the detailed description of the performance of the viscosity measurement, reference is made to the entire contents of WO 2016/061069 A2.

The viscosity of the respective polyvinyl alcohol/polyvinyl acetate copolymer correlates to its molecular weight ("weight-average molecular weight"), which means that the viscosity can also be used to estimate the molecular weight of the polymer.

For example, a polyvinyl alcohol/polyvinyl acetate copolymer having a viscosity from about 3.0 to about 27.0 cP, preferably from about 4.0 to about 24.0 cP, more preferably from about 4.0 to about 23.0 cP and most particularly preferably from about 4.0 to about 15.0 cP (measured in each case at about 20° C. under the conditions described previously) may be used to produce the water-soluble foil.

If a blend of different vinyl alcohol/vinyl acetate copolymers is used, two (or more) different vinyl alcohol/vinyl acetate copolymers may be mixed with each other. The water-soluble foil is then produced from this mixture.

The two polyvinyl alcohol/polyvinyl acetate copolymers may differ from one another for example in terms of their degree of hydrolysis or also in terms of their viscosity (and thus also in terms of their molecular weight).

The molecular weight of a polyvinyl alcohol/polyvinyl acetate copolymer may be for example in a range from about 30,000 to about 170,000 g/mol, preferably from about 30,000 to about 120,000 g/mol and particularly preferably from about 35,000 to about 100,000 g/mol (values given are averages of the molar masses).

The molar mass of the polymer may also be determined with gel permeation chromatography, for example.

A particularly preferred product is therefore exemplified in that
(ia) the water-soluble foil comprises one or more vinyl alcohol/vinyl acetate copolymers having a molecular weight from about 30,000 to about 170.000 g/mol, preferably from about 30,000 to about 120,000 g/mol and particularly preferably from about 35,000 to about 100,000 g/mol (expressed as average molar mass).

The water-soluble foil is most particularly preferably produced from a polymer mixture which comprises a first vinyl alcohol/vinyl acetate copolymer and additionally also a second vinyl alcohol/vinyl acetate copolymer which differs from the first polymer.

In a particularly preferred embodiment, a product as contemplated herein is exemplified in that
(ia) the water-soluble foil comprises a polymer mixture including
(iaa) a first vinyl alcohol/vinyl acetate copolymer and
(iab) a second vinyl alcohol/vinyl acetate copolymer which is different from the first vinyl alcohol/vinyl acetate copolymer (iaa).

According to the present disclosure, the difference between the polymers is understood to mean that the polymers are structurally different, which may be manifested for example in
a different degree of hydrolysis, and/or
a different viscosity (measured under the prescribed conditions) and/or
a different composition of the repeat units.

As was described previously, at least about 50 wt % of a water-soluble foil preferably includes PVOH polymers and/or PVOH copolymers. Besides the PVOH (co)polymers, the foil may also comprise further components. Thus for example the foil may also contain plasticisers, filler materials, crosslinking agents, dyes and/or bitter substances.

The addition of plasticisers may increase the foil's flexibility. Examples of substances that may typically be used as plasticisers are those containing glycerol, diglycerol, sorbitol, ethylene glycol, diethylene glycol, propylene glycol, dipropylene glycol, polyethylene glycols (with a molecular weight up to about 400 g/mol).

The foil may also contain further polymers which may be introduced as fillers, for example. The use of further polymers can have the effect of increasing the foil's resistance to chemicals and/or the substances which are intended to be packed in the pouch chamber.

Other polymers that are usable are for example polysaccharides, such as for example methyl cellulose, carboxymethyl cellulose, ethyl cellulose, hydroxyethyl cellulose, hydroxypropyl cellulose, hydroxypropylmethyl cellulose, dextrin and hydroxypropyl starch, particularly preferably at least one water-soluble polysaccharide from the group of hydroxypropyl starches.

Polyvinyl pyrrolidones (either crosslinked or not crosslinked) may also be introduced as additional polymers.

It is most particularly preferred if the foils also additionally contain at least one polysaccharide.

In a most particularly preferred embodiment, a product as contemplated herein is exemplified in that the water-soluble foil comprises
- (ia) one or more vinyl alcohol/vinyl acetate copolymers and
- (ib) at least one optionally modified polysaccharide, preferably at least one polysaccharide from the group of methyl cellulose, carboxymethyl cellulose, ethyl cellulose, hydroxyethyl cellulose, hydroxypropyl cellulose, hydroxypropylmethyl cellulose, dextrin and hydroxypropyl starch, particularly preferably at least one water-soluble polysaccharide from the group of hydroxypropyl starches.

Further suitable fillers which may be contained in the water-soluble foil are silica, metal oxides, calcium carbonate, talc and mica.

The thickness of the water-soluble foil(s) used to produce the pouch and for packing the shampoo preparation is preferably from about 0.01 to about 0.1 mm, more preferably from about 0.01 to about 0.08 mm and in particular from about 0.02 to about 0.06 mm.

Determination of the Foil's Solubility in Water

The product as contemplated herein comprises a pouch which forms at least one sealed chamber. The wall of the pouch (and thus of the chamber as well) is produced from a water-soluble foil.

The essential element in this context is that the foil is soluble in water, so that the pouch dissolves while the products are in use (for washing the hair or in the shower, for example).

In this context, water-solubility is determined according to the following method: Material
Beaker (600 ml)
Magnetic stirrer (for example Labline model no. 1250 or equiv.) and agitator, 5 cm
Thermometer (0 100° C.)
Stopwatch (0 300 s)
Polaroid 35 mm slide mount
Clamps and stand
Distilled water (20° C.)
Method Pieces with dimensions 3.8×3.2 cm are cut out of the foil whose solubility in water is to be determined. These pieces are placed in the slide mount. The beaker is filled with 500 ml distilled water. The fill height of the glass is marked on the beaker. The beaker is then fixed on the magnetic stirrer, the agitator is added, and the magnetic stirrer is set to a level that generates a vortex in the beaker, such that the vortex occupies a fifth of the original fill height. The slide mount to which the foil is attached is introduced into the beaker with clamps in such a way that the long end of the slide mount is aligned parallel with the surface of the water. In this arrangement, the slide mount should be immersed in the water to such a depth that the upper edge of the slide mount is 0.6 cm below the surface of the moving water. The short side of the slide mount should be positioned beside the wall of the beaker, and the other side should be aligned directly above the agitator.

When the slide mount is immersed in the water, the stopwatch is started. The disintegration of the foil takes place when the foil beaks. As soon as the visible parts of the slide mount have been removed, the slide mount is taken out of the beaker. Dissolution is complete as soon as no more foil fragments are visible and as soon as the solution has become clear.

A foil is water-soluble within the meaning of the present disclosure if the dissolution according to the method described previously is completed within about 300 seconds (measurement conducted at 20° C.).

The foil is preferably dissolved while the measurement is conducted according to the method described previously within about 250 seconds, more preferably within about 200 seconds and particularly preferably within about 150 Seconds.

Production of the Foil and the Pouch

In order to produce the at least one sealed chamber of the pouch, the water-soluble foil described earlier is used, wherein the foil comprises the polymers described earlier.

In this context, for example, the polymers may first be blended with each other—optionally with the use of thermal influence—to produce the polymer blend. Then the foil may be shaped from the polymers or the polymer blend, wherein the forming may be effected for example by casting, extrusion, rolling out or similar.

A pouch is now formed from this foil by moulding at least one sealed chamber from the foil. The chamber may be moulded by methods known to the person skilled in the art. For example, preforms may first be created from the water-soluble foil. These undergo a blown pressure process, wherein the preform is conveyed to various processing stations inside a blow moulding machine. Such a blow moulding machine typically includes a heating device and a blowing device, in the area of which the previously tempered preform is expanded by biaxial orientation to form a receptacle. The expansion is carried out using compressed air which is introduced into the preform that is to be expanded. In one embodiment, the chamber is filled with the shampoo and sealed as it is being formed.

The sealing may take place for example by fusing and applying pressure to the weld joints in the pouch.

Shampoo Composition

A restoring and cleaning shampoo composition is present in at least one sealed chamber of the pouch. An exemplifying feature of the shampoo composition is its low water content and its content of at least one anionic tenside and at least one cationic tenside.

Water Content

In order to stop the water-soluble foil from dissolving too soon, the shampoo formulation as contemplated herein is formulated to contain little or no water. This means that the water content (iia) in the cosmetic shampoo is not more than about 20 wt %. In this context, the water content indicated in wt % is relative to the total quantity of the shampoo.

The lower the water content is in the shampoo composition, the more effectively the undesirable dissolution of the water-soluble foil can be prevented. On the other hand, a certain, low, measured water content may also help to keep the anionic and cationic tensides in solution and prevent them from precipitating. For this reason, it is most particularly preferred to adjust the water content to a very specific low range.

The shampoo preferably contains from about 0 to about 19 wt %, preferably from about 3 to about 19 wt %, more preferably from about 5 to about 19 wt %, more preferably still from about 5 to about 12 wt % and most particularly preferably from about 4 to about 10 wt % water relative to its total weight.

In a further, most particularly preferred embodiment, a product as contemplated herein is exemplified in that the
- (ii) shampoo composition in the sealed chamber of the pouches contains—relative to its total weight
  - (iia) from about 0 to about 19 wt %, preferably from about 3 to about 19 wt %, more preferably from about 5 to about 19 Wt%, still more preferably from about 5 to about 12 wt % and most particularly preferably from about 4 to about 10 wt % water.

Anionic Tensides (iib) and Cationic Tensides (iic)

In order to achieve both a cleaning and a care effect, the shampoo formulation as contemplated herein contains both at least one anionic tenside (iib) and at least one (iic) cationic tenside.

The preparation of the different charged tensides in the anhydrous/low-water shampoo formulation at the same time presents the person skilled in the art with the greatest challenges, in order to prevent the two tensides from being precipitated out of the solution prematurely.

For the solution to this problem, the selection very specific anionic tensides has been found to be most particularly suitable.

For the purposes of the present disclosure, an anionic tenside (b) contains no cationic groups, i.e. zwitterionic tensides are excluded from the definition of an anionic tensidet.

Accordingly, anionic tensides as contemplated herein are exemplified by the presence of a water-solubilising anionic group, e.g., a carboxylate, sulfate, sulfonate or phosphate group and a lipophilic alkyl group having about from about 8 to about 30 C atoms. The molecule may further contain glycol or polyglycol ether groups, ester, ether and amide groups as well as hydroxyl groups.

Typical examples of anionic tensides are alkylbenzene sulfonates, alkane sulfonates, olefin sulfonates, alkylether sulfonates, glycerol ether sulfonates, α-methylester sulfonates, sulfofatty acids, alkyl sulfates, fatty alcohol ether sulfates, glycerol ether sulfates, mixed hydroxyether sulfates, monoglyceride(ether)sulfates, fatty acid amido(ether)sulfates, mono- and dialkyl sulfosuccinates, mono- and dialkyl sulfosuccinamates, sulfotriglycerides, amide soaps, ethercarboxylic acids and salts thereof, fatty acid isethionates, tatty acid sarcosinates, fatty acid taurides, acyl lactylates, acyl tartrates, acyl glutamates, acyl aspartates, alkyl oligoglucoside sulfates, protein fatty acid condensates (particularly wheat-based plant products) and alkyl(ether)phosphates. If the anionic tensides contain polyglycol ether chains, these may include a conventional but preferably limited homologue distribution.

Examples of the anionic tensides that are usable in principle as contemplated herein are, each in the form of the sodium sodium, potassium and ammonium as well as the mono-, di- and trialkanolammonium salts with from about 2 to about 4 C atoms in the alkanol group, linear and branched fatty acids with from about 8 to about 30 C atoms (soaps), ethercarboxylic acids with formula R—O—($CH_2$—$CH_2O)_x$—$CH_2$—COOH, in which R is a linear alkyl group with from about 8 to about 30 C atoms and x=0 or from about 1 to about 16, acyl sarcosides with from about 8 to about 24 C atoms in the acyl group, acyl taurides with from about 8 to about 24 C atoms in the acyl group, acyl isethionates with from about 8 to about 24 C atoms in the acyl group,which are accessible by esterification of fatty acids with the sodium salt of 2-hydroxyethane-sulfonic acid (isethionic acid). If fatty acids with from about 8 to about 24 C atoms are used for this esterification, that is to say for example lauric, myristic, palimitic or stearic acid, or also technical fatty acid fractions e.g., the $C_{12}$-$C_{18}$ fatty acid fraction that can be obtained from coconut fatty acid, the suitable $C_{12}$-$C_{18}$ acyl isethionates preferred as contemplated herein can be prepared, sulfosuccinic acid mono- and -dialkyl esters with from about 8 to about 24 C atoms in the alkyl group and sulfosuccinic acid monoalkylpolyoxyethyl esters with from about 8 to about 24 C atoms in the alkyl group and from about 1 to about 6 oxyethyl groups. Sulfosuccinic acid mono- and dialkyl esters may be prepared by converting maleic acid anhydride to maleic acid monoester of the fatty alcohol with a fatty alcohol having from about 8 to about 24 C atoms and further reaction with sodium sulfite to produce sulfosuccinic acid ester. Particularly suitable sulfosuccinic acid esters are derived from fatty alcohol fractions with from about 12 to about 18 C atoms, such as may be accessed e.g. from coconut fatty acid or coconut fatty acid methylester by hydrogenation, linear alkane sulfonates with from about 8 to about 24 C atoms, linear alpha-olefin sulfonates with from about 8 to about 24 C atoms, alpha-sulfofatty acid methylesters of fatty acids with from about 8 to about 30 C atoms, alkyl sulfates and alkylpolyglycol ether sulfate having formula R—O($CH_2$—$CH_2O)_x$-$OSO_3H$, in which R is a preferably linear alkyl group with from about 8 to about 30 C atoms and x=0 or from about 1 to about 12, hydroxysulfonates substantially corresponding to at least of of the two following formulas or mixtures thereof and salts thereof, $CH_3$—$(CH_2)_y$—CHOH—$(CH_2)_p$—(CH—$SO_3M$)-$(CH_2)_z$—$CH_2$—O—$(C_nH_{2n}O)_x$—H, and/or $CH_3$—$(CH_2)_y$—(CH—$SO_3M$)-$(CH_2)_p$—CHOH—$(CH_2)_z$—$CH_2$—O—$(C_nH_{2n}O)_x$—H wherein in both formulas y and z=0 or integers from about 1 to about 18, p=0, from about 1 or about 2 and the total (y+z+p) is a number from about 12 to about 18, x=0 or a number from about 1 to about 30 and n is an integer from about 2 to about 4 and M=H or an alkaline, particularly sodium, potassium, lithium, alkaline earth , particularly magnesium, calcium, zinc and/or an ammonium ion, which may or may not be substituted, particulary mono-, di-, tri- quaternary ammonium ions with C1 to C4 alkyl, alkenyl or aryl radicals, sulfated hydroxyalkyl polyethylene and/or hydroxyalkylene propylene glycol ethers having formula $R^1$—(CHOSO$_3$M)-CHR$^3$—(OCHR$^4$—CH$_2$)n-OR$^2$ wherein $R^1$ is a linear alkyl radical having from about 1 to about 24 C atoms, $R^2$ stands for a linear or branched, saturated alkyl radical with from about 1 to about 24 C atoms, $R^3$ stands for hydrogen or a linear alkyl radical with from about 1 to about 24 C atoms, $R^4$ stands for hydrogen or a methyl radical and M for hydrogen, ammonium, alkyl ammonium, alkanol ammonium, wherein the alkyl and alkanol radicals each have from about 1 to about 4 C atoms, or a metal atom selected from lithium, sodium, potassium, calcium or magnesium and n stands for a number in the range from about 0 to about 12, and the total number of C atoms contained in $R^1$ and $R^3$ is from about 2 to about 44, sulfonates of unsaturated fatty acids with from about 8 to about 24 C atoms and from about 1 to about 6 double bonds, esters of tartaric acid and citric acid with alcohols, representing adducts of from about 2 to about 15 molecules of ethylene oxide and/or propylene oxide to fatty alcohols with from about 8 to about 22 C atoms, alkyl and/or alkenyl etherphosphates having formula R$^1$(OCH$_2$CH$_2$)$_n$—O—(PO—OX)—OR$^2$, in which R$^1$ preferably stands for an aliphatic hydrocarbon radical with from about 8 to about 30 carbon atoms, R$^2$ stands for hydrogen, a radical (CH$_2$CH$_2$O)$_n$R$^2$ or X, n stands for numbers from about 1 to about 10 and X stands for hydrogen, an alkaline or alkaline earth metal or NR$^3$R$^4$R$^5$R$^6$, wherein R$^3$ to R$^6$ independently of each other represent hydrogen or a C$_1$ to C$_4$ hydrocarbon radical, sulfated fatty acid alkylene glycol esters having formula RCO(AlkO)$_n$SO$_3$M in which RCO— stands for a linear or branched aliphatic, saturated and/or unsaturated acyl radical with from about 6 to about 22 C atoms, Alk stands for CH$_2$CH$_2$, CHCH$_3$CH$_2$ and/or CH$_2$CHCH$_3$, n stands for numbers from about 0.5 to about 5, and M stands for a metal such as an alkaline metal, in particular sodium, potassium, lithium, alkaline earth metal, in particular magnesium, calcium, zinc or ammonium ion, such as $^+$NR$^3$R$^4$R$^5$R$^6$, wherein R$^3$ to R$^6$ wherein R$^3$ to R$^6$ independently of each other represent hydrogen or a C$_1$ to C$_4$ hydrocarbon radical, monoglyceride sulfates and monoglyceride ether sulfates having formula R$^8$OC—(OCH$_2$CH$_2$)$_x$—OCH$_2$—[CHO (CH$_2$CH$_2$O)$_y$H]—CH$_2$O(CH$_2$CH$_2$O)$_z$-SO$_3$X, in which R$^8$CO stands for a linear or branched acyl radical with from about 6 to about 22 carbon atoms, the combined sum of x, y and z stands for 0 or numbers from about 1 to about 30, more preferably from about 2 to about 10, and X stands for an alkaline or alkaline earth meta. Typical examples of monoglyceride(ether)sulfates suitable for the purposes of the present disclosure are the products of conversion of lauric acid monoglyceride, coconut fatty acid monoglyceride, palmitic acid monoglyceride, stearic acid monoglyceried, oleic acid monoglyceride and tallow fatty acid monoglyceride and the ethylene oxide adducts thereof with sulfur trioxide or chlorosulfuric acid in the form of its sodium salts. More preferably, monoglyceride sulfates are used in which the R$^8$CO stands for a linear acyl radical with from about 8 to about 18 carbon atoms, amidoether carboxylic acids, R$^2$—CO—NR$^2$—CH$_2$CH$_2$—O—(CH$_2$CH$_2$O)$_n$CH$_2$COOM, with R$^1$ as a straight-chain or branched alkyl or alkenyl radical having a number of carbon atoms from about 2 to about 30 in the chain, n stands for an integer from about 1 to about 20 and R$^2$ stands for hydrogen, a methyl, ethyl, propyl, isopropyl, n-butyl, t-butyl or isobutyl radical and M stands for hydrogen or a metal such as an alkaline metal, in particular sodium, potassium, lithium, alkaline earth metal, in particular magnesium, calcium, zinc, or an ammonium ion such as $^+$NR$^3$R$^4$R$^5$R$^6$, wherein R$^3$ to R$^6$ are independent of each other and stand for hydrogen or a C1 to C4 hydrocarbon radical. Such products are available commercially for example from the company Chem-Y with the product name Akypo® erhältlich, and acyl glutamates having formula XOOC—CH2CH2CH(C(NH)OR)—COOX, in which RCO stands for a linear or branched acyl radical with from about 6 to about 22 carbon atoms and 0 and/or 1, 2 or 3 double bonds, and X stands for hydrogen, ein an alkaline and/or alkaline earth metal, ammonium, alkyl ammonium, alkanol ammonium or glucammonium.

When a formulation containing little or no water is prepared, the anionic tensides must be particularly compatible with the cationic tensides, i.e. it must be possible to use of the anionic and cationic tensides together in relatively large quantities without the risk of the tensides precipitating undesirably.

Linear alkyl sulfates with from about 8 to about 30 C atoms, alpha-olefin sulfonates with from about 8 to about 30 C atoms and alkyl polyglycol ether sulfates have proven to be particularly compatible with cationic tensides. The tensides in this substance class are anionic tensides with formula (An 1)

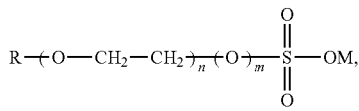

(An 1)

wherein
R stands for a linear or branched, saturated or unsaturated C$_8$-C$_{30}$ alkyl group,
n stands for an integer from about 0 to about 20, preferably an integer from about 0 to about 6,
m stands for 0 or 1,
M stands for hydrogen or a metal such as alkaline metal, in particular sodium, potassium, lithium, alkaline earth metal, in particular magnesium, calcium, zinc, an ammonium ion (NH$_4$)$_+$, a HN(CH$_2$CH$_2$OH)$_3$$^+$ on or a HN(CH$_2$CH(OH)CH$_3$$^-$ ion.

In a most particularly preferred embodiment, a product as contemplated herein is exemplified in that the shampoo composition inside the sealed chamber of the pouch
(iib) contains at least one anionic tenside having formula (An 1),

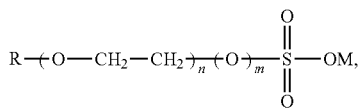

(An 1)

wherein
R stands for a linear or branched, saturated or unsaturated C$_8$-C$_{30}$ alkyl group,
n stands for an integer from about 0 to about 20, preferably an integer from about 0 to about 6,
m stands for 0 or 1,
M stands for hydrogen or a metal such as alkaline metal, in particular sodium, potassium, lithium, alkaline earth metal, in particular magnesium, calcium, zinc, an ammonium ion (NH$_4$)$^+$, a HN(CH$_2$CH$_2$OH)$_3$$^+$ ion or a HN(CH$_2$CH(OH)CH$_3$)$_3$$^+$ ion.

Radical R stands for a linear or branched, saturated or unsaturated C$_8$-C$_{30}$ alkyl group.

Radical R preferably stands for a linear, saturated or unsaturated C$_{12}$-C$_{18}$ alkyl group.

Examples of saturated C$_{12}$-C$_{18}$ alkyl groups are e.g. a lauryl group, a myristyl group, a cetyl group or a stearyl group.

An unsaturated C$_{12}$-C$_{18}$ alkyl group may include one or more double bonds. Most particularly preferable is a mono-unsaturated C$_{12}$-C$_{18}$ alkyl group (which may then also be described alternatively as an alkenyl group).

The radical n stands for an integer from about 0 to about 20, preferably for an integer from about 0 to about 6. Thus, n indicates the number of ethoxy groups contained in the anionic tenside. If n stands for 0, the anionic tenside of formula (An 1) is not ethoxylated, an alkyl sulfate, alkenyl sulfate, alkyl sulfonate or alkenyl sulfonate (or salts thereof) is present.

The radical m stands for 0 or 1. If n is equal to 0 and m is equal to 0, an alkyl sulfonate or alkenyl sulfonate (or salts thereof) is present.

In a most particularly preferred embodiment, a product as contemplated herein is also exemplified in that the shampoo composition in the sealed chamber of the pouch
(iib) contains at least one anionic tenside having formula (An 2),

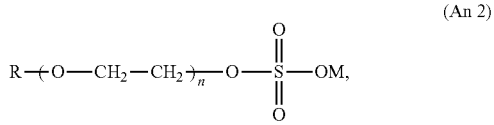

(An 2)

wherein
R stands for a linear or branched, saturated or unsaturated $C_8$-$C_{30}$ alkyl group,
n stands for an integer from about 0 to about 20, preferably from about 0 to about 6, and
M stands for hydrogen or a metal such as alkaline metal, in particular sodium, potassium, lithium, alkaline earth metal, in particular magnesium, calcium, zinc, an ammonium ion $(NH_4)^+$, a $HN(CH_2CH_2OH)_3^+$ ion or a $HN(CH_2CH(OH)CH_3)_3^+$ ion.

As part of a most particular embodiment, of the anionic tensides having formula (An 1), the ones particularly preferred are those in which
R stands for a linear, saturated or unsaturated $C_{12}$-$C_{18}$ alkyl group,
n stands for 0,
m stands for 0, and
M stands for hydrogen or a metal such as alkaline metal, in particular sodium, potassium, lithium, alkaline earth metal, in particular magnesium, calcium, zinc, or an ammonium ion $(NH_4)^+$ or a $HN(CH(CH_3)_2)_3^+$ ion.

In a most particularly preferred embodiment, a product as contemplated herein is exemplified in that the shampoo composition in the sealed chamber of the pouch
(iib) contains at least one anionic tenside having formula (An 1),

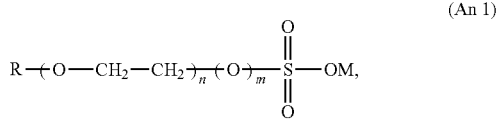

(An 1)

wherein
R stands for a linear, saturated or unsaturated $C_{12}$-$C_{18}$ alkyl group,
n stands for 0,
m stands for 0, and
M stands for hydrogen or a metal such as alkaline metal, in particular sodium, potassium, lithium, alkaline earth metal, in particular magnesium, calcium, zinc, or an ammonium ion $(NH_4)^+$ a $HN(CH_2CH_2OH)_3^+$ ion or a $HN(CH_2CH(OH)CH_3)_3^+$ ion.

When n is equal to 0 and m is equal to 0, an anionic is present with formula (An 3)

(An 3)

wherein
R stands for a linear, saturated or unsaturated $C_{12}$-$C_{18}$ alkyl group, and
M stands for hydrogen or a metal such as alkaline metal, in particular sodium, potassium, lithium, alkaline earth metal, in particular magnesium, calcium, zinc, or an ammonium ion $(NH_4)^+$ a $HN(CH_2CH_2OH)_3^+$ ion or a $HN(CH_2CH(OH)CH_3)_3^+$ ion.

Anionic tensides having formula (An 3) are alkyl sulfonates or alkenyl sulfonates (or salts thereof).

Particularly preferred anionic tensides having formulas (An 1) to (An 3) are for example
sodium laureth sulfate
TIPA laureth sulfate, such as is marketed commercially by the company Schimmer & Schwarz for example with the brand names Zetesol TP 300 and Zetesol TP 200 (TIPA=triisopropanolammonium)
sodium cetearyl sulfate
sodium ($C_{14}$-$C_{16}$)-alpha olefin sulfonate, such as is marketed commercially with the brand name Hostapur OSB for example.

A cleaning effect can be obtained with relatively small active quantities of anionic tensides. But if the cleaning effect is intended to be particularly powerful, the active quantities of anionic are increased accordingly.

The shampoo may contain one or more anionic tensides—particularly the aforementioned preferred and particularly preferred representatives—in a total quantity from about 1 to about 30 wt %. All quantities indicated in wt % in this context are stated relative to the total quantity of the shampoo formulation.

However, it is preferred to use the anionic tensides in larger total quantities from about 8 to about 40 wt %, preferably from about 10 to about 35 wt %, more preferably from about 12 to about 30 wt % and most particularly preferably from about 14 to about 25 wt %.

In a most particularly preferred embodiment, a product as contemplated herein is exemplified in that the shampoo composition in the sealed chamber of the pouch contains—relative to the total weight of the shampoo composition
(iib) one or more anionic tensides in a total quantity from about 8 to about 40 wt %, preferably from about 10 to about 35 wt %, more preferably from about 12 to about 30 wt % and most particularly preferably from about 14 to about 25 wt %.

In a further most particularly preferred embodiment, a product as contemplated herein is exemplified in that the shampoo composition in the sealed chamber of the pouch contains—relative to the total weight of the shampoo composition
(iib) one or more anionic tensides having formula (An 1) in a total quantity from about 10 to about 40 wt %, preferably from about 12 to about 35 wt %, more preferably from about 14 to about 30 wt % and most particularly preferably from about 16 to about 25 wt %,

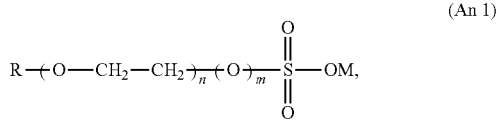

(An 1)

wherein
R stands for a linear or branched, saturated or unsaturated $C_8$-$C_{30}$ alkyl group,
n stands for an integer from about 0 to about 20, preferably an integer from about 0 to about 6,
m stands for 0 or 1,
M stands for hydrogen or a metal such as alkaline metal, in particular sodium, potassium, lithium, alkaline earth metal, in particular magnesium, calcium, zinc, an ammonium ion $(NH_4)^+$ a $HN(CH_2CH_2OH)_3^+$ ion or a $HN(CH_2CH(OH)CH_3)_3^+$ ion.

When the product as contemplated herein is applied to keratinous fibres (hair), an additional care effect should also be obtained besides the cleaning effect. In order to achieve the care effect, the shampoo as contemplated herein also contains at least one cationic tenside (iic).

The one or more cationic tensides (iic) must also be adjusted for use in the shampoo formulation containing little or no water, i.e., it must be possible for the cationic tensides to dissolve as fully as possible in the medium containing little or no water, or at least to be disperse as finely as possible without forming a precipitate or solid substance either alone or in interaction with the anionic tensides.

The term cationic tensides is understood to refer to tensides, that is to say surface-active compounds which each have one or more positive charges. Cationic tensides only have positive charges. These tensides typically have a hydrophobic portion and a hydrophilic head group, wherein the hydrophobic portion usually includes a hydrocarbon skeleton (e.g., includes one or two linear or branched alkyl chains), and the positive charge(s) reside(s) in the hydrophilic head group.

Examples of cationic tensides are
quaternary ammonium compounds, which as hydrophobic radicals may support one or two alkyl chains having a chain length from about 8 to about 28 C atoms
quaternary phosphonium salts, substituted with one or more alkyl chains having a chain length from about 8 to about 28 C atoms or
tertiary sulfonium salts.

The cationic charge in the form of an onium structure may also be part of a heterocyclic ring (e.g., an imidazolium ring or a pyridinium ring).

Besides the functional unit which carries the cationic charge, the cationic tenside may also contain additional uncharged functional groups, this is the case with esterquats, for example.

Preferred cationic tensides having formula (I) are for example physiologically tolerable salts of N,N,N-trimethyl-1-hexadecanaminium, in particular N,N,N-trimethyl-1-hexadecanaminium chloride, which is also marketed with the trade name Dehyquart A-CA. Also preferred are salts of trimethyl stearyl ammonium, in particular trimethylstearyl ammonium chloride, which is also commercially available under the trade name Genamin STAC. Further particularly preferred cationic tensides having formula (I) are salts of trimethyl-1-eicosanaminium, in particular trimethyl-1-eicosanaminium chloride, and salts of trimethyl-1-docosanaminium, in particular trimethyl-1-docosanaminium chloride. A mixture of the two compounds is available from the company Clariant under the trade name Genamin KDMP.

In the course of the work which led to the present disclosure, it was discovered that certain cationic tensides can be incorporated most particularly well in the formulation containing little or no water and are have most particularly good compatibility with the anionic tensides described previously.

Within the group of cationic tensides (iic), the cationic ammonium compounds having formula (Kat 1) have proven to be particularly suitable due to their excellent compatibility with the anionic tensides contained in the shampoo,

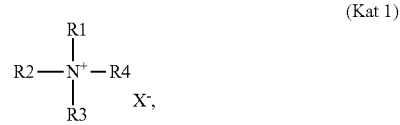

(Kat 1)

wherein
R1, R3, R4 are independent of each other and each stands for a $C_1$-$C_6$ alkyl group, a $C_2$-$C_6$-alkenyl group or a $C_2$-$C_6$ hydroxyalkyl group
R2 stands for a grouping having formula (Kat 2) or for a $C_8$-$C_{30}$ alkyl group

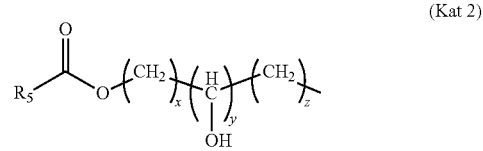

(Kat 2)

wherein
R5 stands for a $C_8$-$C_{30}$ alkyl group,
x stands for an integer from about 0 to about 6,
y stands for an integer from about 0 to about 6, and
z stands for an integer from about 0 to about 6, and
the sum of x+y+z is an integer from about 2 to about 18, and
X— stands for a physiologically tolerable anion.

In a most particularly preferred embodiment, a product as contemplated herein is exemplified in that the shampoo composition in the sealed chamber of the pouch contains—relative to the total weight of the shampoo composition
(iic) one or more cationic tensides having formula (Kat 1)

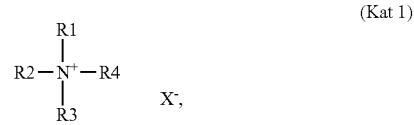

(Kat 1)

wherein
R1, R3, R4 are independent of each other and each stands for a $C_1$-$C_6$ alkyl group, a $C_2$-$C_6$-alkenyl group or a $C_2$-$C_6$ hydroxyalkyl group
R2 stands for a grouping having formula (Kat 2) or for a $C_8$-$C_{30}$ alkyl group

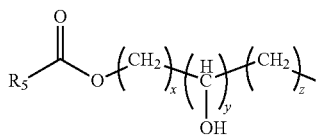
(Kat 2)

wherein
R5 stands for a $C_8$-$C_{30}$ alkyl group,
x stands for an integer from about 0 to about 6,
y stands for an integer from about 0 to about 6, and
z stands for an integer from about 0 to about 6, and
the sum of x+y+z is an integer from about 2 to about 18, and
X— stands for a physiologically tolerable anion.

Radicals R1, R3 and R4 are independent of each other and stand for a $C_1$-$C_6$-alkyl group, a $C_2$-$C_6$ alkenyl group or a $C_2$-$C_6$ hydroxyalkyl group.

Examples of a $C_1$-$C_6$ alkyl group are the methyl, ethyl, propyl, isopropyl, n-butyl, s-butyl and t-butyl, n-pentyl and n-hexyl groups. Propyl, ethyl and methyl are preferred alkyl radicals. Examples of a $C_2$-$C_6$ alkenyl group are vinyl, allyl, but-2-enyl, but-3-enyl and isobutenyl, preferred $C_2$-$C_6$ alkenyl radicals are vinyl and allyl. Preferred examples of a hydroxy-$C_1$-$C_6$-alkyl group are a hydroxymethyl, a 2-hydroxyethyl-, a 2-hydroxypropyl, a 3-hydroxypropyl, a 4-hydroxybutyl group, a 5-hydroxypentyl and a 6-hydroxyhexyl group. Radicals R1, R3 and R4 are independent of each other and stand for a $C_1$-$C_6$-alkyl group. Radicals R1, R3 and R4 particularly preferably stand for a methyl group.

Radical R2 stands for a grouping having formula (Kat 2) or for a $C_8$-$C_{30}$ alkyl group. Radical R2 particularly preferably stands for a grouping having formula (Kat 2).

If radical R2 stands for a grouping with formula (Kat 2), the cationic tenside forms a compound having formula (Kat 3)

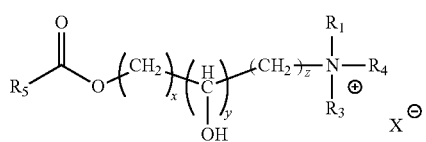
(Kat 3)

wherein the radicals R1, R3 R4 and R5 may stand for the substituents described previously.

The cationic tensides having formula (Kat 3) are most particularly preferably used in the cosmetic products as contemplated herein

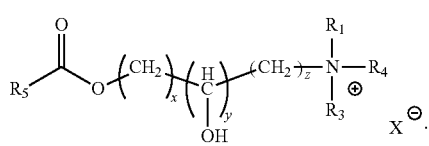
(Kat 3)

Radical R5 stands for a $C_8$-$C_{30}$ alkyl group. Radical R5 preferably stands for a $C_{12}$-$C_{30}$ alkyl group, more preferably for a $C_{14}$-$C_{30}$ alkyl group, still more preferably for a $C_{16}$-$C_{30}$ alkyl group, yet more preferably for a $C_{18}$-$C_{30}$ alkyl group and most particularly preferably for a $C_{20}$-$C_{30}$ alkyl group.

x stands for an integer from about 0 to about 6. Preferably, x stands for 0, 1 or 2.
y stands for an integer from about 0 to about 6. Preferably, y stands for 0, 1 or 2.
z stands for an integer from about 0 to about 6. Preferably, z stands for 0 or 1.

Here too, the parameters are subject to the requirement that the sum of x+y+z is an integer of at least 2.

In each case, $X^-$ stands for a physiologically tolerable anion. Suitable physiologically tolerable anions are halide, hydrogen sulfate, sulfate, benzene sulfonate, p-toluene sulfonate, acetate, citrate, lactate, tartrate, methyl sulfate ($H_3COSO_3^-$), methyl sulfonate or trifluoromethane sulfonate. Particularly preferably, $A^-$ stands for chloride, bromide or methyl sulfate ($H_3COSO_3^-$).

In a most particularly preferred embodiment, a product as contemplated herein is exemplified in that the shampoo composition in the sealed chamber of the pouch contains—relative to the total weight of the shampoo composition
(iic) one or more cationic tensides having formula (Kat 3)

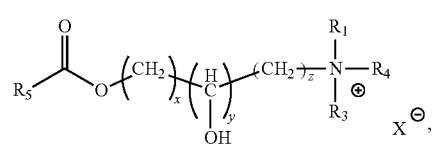
(Kat 3)

wherein
R5 stands for a $C_{12}$-$C_{30}$ alkyl group, more preferably for a $C_{14}$-$C_{30}$ alkyl group, still more preferably for a $C_{16}$-$C_{30}$ alkyl group, more preferably still for a $C_{18}$-$C_{30}$ alkyl group, and most particularly preferably for a $C_{20}$-$C_{30}$ alkyl group,
x stands for 0, 1 or 2
y stands for 0 or 1
z stands for 0, 1 or 2,
wherein the sum of x+y+z is an integer from 2 to 5, and
R1, R3 and R4 are independent of each other and stand for a $C_1$-$C_6$ methyl group, in particular a methyl group.

A most particularly preferred cationic tenside with formula (Kat 3) is for example [3-(behenoyloxy)-2-hydroxypropyl]trimethylammonium chloride (INCI=BEHENOYL PG-TRIMONIUM CHLORIDE), which is marketed commercially under the trade names Quartamin BTC 131 or Akypo Quat 131 by KAO Chemicals (Inter-Harz).

The one or more cationic tensides is/are also most particularly preferably used in the shampoo composition as contemplated herein in specified quantity ranges.

The shampoo may contain one or more anionic tensides—particularly the aforementioned preferred and particularly preferred representatives—in a total quantity from about 0.1 to about 10 wt %. All quantities indicated in wt % in this context are stated relative to the total quantity of the shampoo formulation.

However, it is preferred to use the cationic tensides in total quantities from about 0.2 to about 9.0 wt %, preferably from about 0.3 to about 8.0 wt %, more preferably from about 0.4 to about 7.0 wt % and most particularly preferably from about 0.4 to about 6.0 wt %.

In a most particularly preferred embodiment, a product as contemplated herein is exemplified in that the shampoo composition in the sealed chamber of the pouch contains—relative to the total weight of the shampoo composition (iic) one or more cationic tensides in a total quantity from about 0.2 to about 9.0 wt %, preferably from about 0.3 to about 8.0 wt %, more preferably from about 0.4 to about 7.0 wt % and most particularly preferably from about 0.4 to about 6.0 wt %.

Solvents

The shampoo composition as contemplated herein is prepared with little or no water. This means that preferably solvents and/or short-chain alcohols may be used as the cosmetic carrier.

For example alcohols with from about 2 to about 9 C atoms and from about 1 to about 6 hydroxy groups may be used as short-chain alcohols.

The alcohol with from about 2 to about 9 carbon atoms and from about 1 to about 6 hydroxyl groups is preferably selected from at least one compound in the group of glycerol, 1,2-propanediol, 1,3-propanediol, ethanol, ethylene glycol, isopropanol, n-butanol, 1,3-butylene glycol. Particularly preferred alcohols are 1,2-propanediol, 1,3-propanediol and glycerol.

In a most particularly preferred embodiment, a product as contemplated herein is exemplified in that the shampoo composition in the sealed chamber of the pouch contains one or more alcohols with from about 2 to about 9 C atoms and from about 1 to about 6 hydroxy groups preferably selected from the group of glycerol, 1,2-propanediol, 1,3-propanediol, ethanol, ethylene glycol, isopropanol n-butanol, and/or 1,3-butylene glycol.

The one or more alcohols constitute the carrier base of the shampoo formulation and are therefore preferably contained in larger quantity ranges in the shampoo formulation. The shampoo formulation preferably contains—relative to its total weight—one or more alcohols with from about 2 to about 9 carbon atoms and from about 1 to about 6 hydroxyl groups in a total quantity from about 10 to about 80 wt %, preferably from about 15 to about 70 wt %, more preferably from about 20 to about 60 wt % and most particularly preferably from about 25 to about 50 wt %.

In a most particularly preferred embodiment, a product as contemplated herein is exemplified in that the shampoo composition in the sealed chamber of the pouch contains—relative to the total weight of the shampoo composition—one or more alcohols with from about 2 to about 9 carbon atoms and from about 1 to about 6 hydroxyl groups in a total quantity from about 10 to about 80 wt %, preferably from about 15 to about 70 wt %, more preferably from about 20 to about 60 wt % and most particularly preferably from about 25 to about 50 wt %.

Further Fatty Components

In order to reinforce the conditioning effect, one or more additional fatty components may also be used in the shampoo composition as contemplated herein. In addition, the fatty components may also be part of the cosmetic carrier base.

For the purposes of the present disclosure, the term "fatty components" is understood to include organic compounds with a solubility in water at room temperature (22° C.) and atmospheric pressure (760 mmHg) less than about 1 wt %, preferably less than about 0.1 wt %. The definition of fatty components explicitly comprises only uncharged (i.e., non-ionic) compounds. Fatty components contain at least one saturated or unsaturated alkyl group with at least about 8 C atoms. The molecular weight of the fatty components is not more than about 5000 g/mol, preferably not more than about 2500 g/mol, and particularly preferably not more than about 1000 g/mol. The fatty components are neither polyoxyalkylated nor polyglycylated compounds.

In this context, the components from the group of $C_8$-$C_{30}$ fatty alcohols, $C_8$-$C_{30}$ fatty acid triglycerides, and/or hydrocarbons are understood to be preferred fatty components. For the purposes of the present disclosure, explicitly only non-ionic substances are considered as fatty components. Charged compounds such as fatty acids and salts thereof for example are not considered as fatty components.

The C8-C30 fatty alcohols may be saturated, mono- or polyunsaturated, linear or branched fatty alcohols with from about 8 to about 30 C atoms.

Examples of preferred linear, saturated C8-C30 fatty alcohols are octan-1-ol, decan-1-ol, dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear, unsaturated fatty alcohols are (9Z)-octadec-9-en-1-ol (oleyl alcohol), (9E)-octadec-9-en-1-ol (elaidyl alcohol), (9Z,12Z)-octadeca-9,12-diene-1-ol (linoleyl alcohol), (9Z,12Z,15Z)-octadeca-9,12,15-triene-1-ol (linolenoyl alcohol), gadoleyl alcohol ((9Z)-eicos-9-en-1-ol), arachidonic alcohol ((5Z,8Z,11Z,14Z)-eicosa-5,8,11,14-tetraene-1-ol), erucyl alcohol ((13Z)-docos-13-en-1-ol) and/or brassidyl alcohol ((13E)-docosen-1-ol).

For the purposes of the present disclosure, a $C_8$-$C_{30}$ fatty acid triglyceride is understood to be the triester of the trivalent alcohol glycerol with three equivalent fatty acids. In this context, both structurally identical and different fatty acids may be involved in the ester formations in a triglyceride molecule.

For the purposes of the present disclosure, fatty acids are understood to be saturated or unsaturated, unbranched or branched, unsubstituted or substituted $C_8$-$C_{30}$ carboxylic acids. Unsaturated fatty acids may be mono- or polyunsaturated. In an unsaturated fatty acid, the one or more C—C double bond(s) thereof may be cis- or trans-configured.

The fatty acid triglycerides that are noteworthy for being particularly suitable are those in which at least one of the ester groups is formed on the basis of glycerol with a fatty acid selected from octanoic acid (caprylic acid), decanoic acid (capric acid), dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachic acid) docosanoic acid (behenic acid), petroselic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetranoic acid] and/or nervonic acid [(15Z)-tetracos-15-enoic acid].

The fatty acid triglycerides may also be of natural origin. The fatty acid triglycerides and mixtures thereof that occur in soy oil, peanut oil, olive oil, sunflower oil, macadamia nut oil, moringa oil, apricot kernel oil, marula oil and/or optionally castor oil are particularly suitable for use in the product as contemplated herein.

Hydrocarbons are compounds solely including carbon and hydrogen atoms, with from about 8 to about 80 C atoms. In this context, aliphatic hydrocarbons such as mineral oils, liquid paraffin oils (e.g., paraffinum liquidum or paraffinum perliquidum), isoparaffin oils, semisolid paraffin oils, paraffin waxes, hard paraffin (paraffinum solidum), vaseline and polydecenes are particularly preferred in this context.

In this context, liquid paraffin oils (paraffinum liquidum and paraffinum perliquidum) have proven particularly suitable. The hydrocarbon is most particularly preferably paraffinum liquidum, also called liquid paraffin. Paraffinum liquidum is a mixture of purified, saturated aliphatic hydrocarbons which includes mainly hydrocarbon chains with a C chain distribution of from about 25 to about 35 C atoms.

In a most particularly preferred embodiment, a product as contemplated herein is exemplified in that the shampoo composition in the sealed chamber of the pouch contains one or more fatty components from the group of $C_8$-$C_{30}$ fatty alcohols, $C_8$-$C_{30}$ fatty acid triglycerides, and/or hydrocarbons.

The one or more fatty components are preferably contained in the shampoo composition as contemplated herein in specific quantity ranges.

The shampoo composition contains—relative to its total weight—one or more fatty components in a total quantity from about 5 to about 30 wt %, preferably from about 8 to about 28 wt %, more preferably from about 10 to about 25 wt % and most particularly preferably from about 15 to about 22 wt %.

In a most particularly preferred embodiment, a product as contemplated herein is exemplified in that the shampoo composition in the sealed chamber of the pouch contains—relative to the total weight of the shampoo composition—one or more fatty components in a total quantity from about 5 to about 30 wt %, preferably from about 8 to about 28 wt %, more preferably from about 10 to about 25 wt % and most particularly preferably from about 15 to about 22 wt %

Further Formulation Components

It has further proven advantageous if the shampoos contain non-ionogenic surfactants. Non-ionic tensides are alkyl polyglycosides and alkylene oxide adducts to fatty alcohols and fatty acids, each with from about 2 to about 30 mol ethylene oxide per mol fatty alcohol or fatty acid have proven preferable. Preparations with outstanding properties are also obtained if they contain fatty acid esters of ethoxylated glycerol as the non-ionic tensides.

The non-ionic, zwitterionic or amphoteric tensides are used in proportions from about 0.1 to about 45 wt %, preferably from about 1 to about 30 wt % and most particularly preferably from about 1 to about 15 wt %, relative to the total quantity of the application-ready media.

The shampoos as contemplated herein may also contain further active, auxiliary and additive substances such as non-ionic polymers, for example vinyl pyrrolidin-one/vinylacrylate copolymers, polyvinylpyrrolidinone, vinylpyrrolidinone/vinyl acetate copolymers, polyethylene glycols and polysiloxanes; additional silicones such as volatile or non-volatile, straight-chain, branched or cyclic, crosslinked or non-crosslinked polyalkylsiloxanes (such as dimethicone or cyclomethicone), polyarylsiloxanes and/or polyalkylarylsiloxanes, in particular polysiloxanes with organofunctional groups, such as substituted or unsubstituted amines (amodimethicone), carboxyl-, alkoxy- and/or hydroxyl groups (dimethicone copolyols), linear polysiloxane (A)-polyoxyalkylene (B) block copolymers, grafted silicone polymers; cationic polymers such as quaternised cellulose ethers, polysiloxanes with quaternary groups, dimethyldiallyl ammonium chloride polymers, acryl-amide-dimethyldiallyl ammonium chloride copolymers, dimethylamino-ethylmethacrylate-vinylpyrrolidinone copolymers quaternised with diethyl sulfate, vinylpyrrolidinone-imidazolinium-methochloride copolymers and quaternised polyvinyl alcohol; zwitterionic and amphoteric polymers; anionic polymers such as for example polyacrylic acids or crosslinked polyacrylic acids; structuring substances such as glucose, maleic acid and lactic aid, hair conditioning compounds such as phospholipids, for example lecithin and cephalins; perfume oils, dimethyl isosorbide and cyclodextrine; agents for improving fibre structure, in particular mono-, di- and oligosaccharides such as glucose, galactose, fructose, fruit sugar and lactose; dyes for colouring the medium; antidandruff agents such as piroctone olamine, zinc omadine and climbazol; amino acids and oligopeptides; animal- and/or plant-based protein hydrolysates, and in the form of fatty acid condensation products thereof or optionally anionically or cationically modified derivatives; vegetable oils; light protection products and UV blockers; active agents such as panthenol, pantothenic acid, pantolactone, allantoin, pyrrolidinone carboxylic acids and salts thereof, also bisabolol; polyphenols, in particular hydroycinnamic acids, 6,7-dihydroxycoumarine, hydroxybenzoic acids, catechins, tannins, leukoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; bulking and penetrating agents such as glycerol, propylene glycol monoethyl ethers, carbonates, hydrogen carbonates, guanidines, ureas and primary, secondary and tertiary phosphates; opacifiers such as latex, styrene/PVP- and styrene/acrylamide copolymers; pearl shine agents such as ethylene glycol mono- and -distearate and PEG-3-distearate; pigments and propellants such as propane-butane mixtures, $N_2O$, dimethyl ethers, $CO_2$ and air.

The person skilled in the art will make select these further substances depending on the desired properties of the media. Regarding further optional components and the quantities of such components that are to be used, explicit reference is herewith made to the pertinent reference works known to the person skilled in the art. The additional active and auxiliary substances are preferably added to the media as contemplated herein in quantities from about 0.0001 to about 25 wt %, in particular from about 0.0005 to about 15 wt % in each case, and in case relative to the total weight of the dye preparation (K1) and/or oxidising agent preparation (K2).

Application

The product as contemplated herein is preferably used by the consumer to clean and care for his/her hair. For this purpose, the product is moistened with water, whereupon the water-soluble foil dissolves and releases the shampoo composition. The foil typically dissolved within about 15 seconds to a few minutes. The user can assist the dissolution mechanically, for example by rubbing the product with his/her hands. The, the shampoo is applied to the hair, allowed to take effect briefly or briefly massaged into the skin, and then rinsed out again with water.

A second object is a method for cleaning and caring for the hair, wherein a cosmetic product such as has been disclosed in detail in the description of the first object of the present disclosure is mixed with water, applied to the hair and after an exposure period of from about 10 seconds to about 10 minutes is rinsed out again.

The preceding notes and explanations regarding the product as contemplated herein apply mutatis mutandis to preferred embodiments of the method as contemplated herein.

EXAMPLES

The shampoo preparations listed in the following tables were produced (all figures in wt %):

|  | Ex. 1 | Ex. 2 | Ex. 3 | Ex. 4 |
|---|---|---|---|---|
| Capric acid/Caprylic acid triglyceride | 20.0 | 20.0 | — | 39.5 |
| Stearic acid | 3.0 | 3.0 | 3.0 | 3.0 |
| Water | 15.0 | 10.0 | 15.0 | 10.0 |
| Citric acid | 1.0 | 1.0 | 1.0 | 1.0 |
| Glycerol | — | — | 39.0 | — |
| Sodium-$C_{14}$-$C_{16}$-olefin-sulfonate | 12.0 | — | 12.0 | 12.0 |
| TIPA-laureth-sulfate (triisopropanol ammonium $C_{12}$-fatty alcohol ether sulfate, CAS no. 89952-33-0) | 6.0 | 12.0 | — | — |
| Sunflower seed oil PEG-8 ester | 6.0 | 6.0 | 6.0 | — |
| Betaine | 6.0 | 6.0 | — | 6.0 |
| Quatrnium-96 | 2.5 | 2.5 | — | — |
| [3-(behenoyloxy)-2-hydroxypropyl] trimethylammonium chloride (Quartamin BTC-131, CAS no. 69537-38-8) | 0.5 | 0.5 | 0.5 | 0.5 |
| 1,3-propanediol | to 100 | to 100 | — | — |
| 1,2-propanediol | — | — | to 100 | to 100 |

The preparations of examples 1 to 4 were packed in a single-chamber receptacle (pouch) made of a water-soluble foil from the company Monosol, type LX 9643 (Monosol, type LX 9643: water-soluble foil, comprising polyvinyl alcohol/polyvinyl acetate copolymer, degree of hydrolysis approx. 84%, average molar mass=39,000 g/mol)

|  | Ex. 5 | Ex. 6 | Ex. 7 | Ex. 8 |
|---|---|---|---|---|
| Capric acid/Caprylic acid triglyceride | 20.0 | 20.0 | — | 39.5 |
| Stearic acid | 8.0 | 10.0 | 8.0 | 10.0 |
| Water | 1.0 | 1.0 | 1.0 | 1.0 |
| Citric acid | — | — | 39.0 | — |
| Glycerol | 14.0 | — | 16.0 | 10.0 |
| Sodium-$C_{14}$-$C_{16}$-olefin-sulfonate | 6.0 | 15.0 | — | 10.0 |
| TIPA-laureth-sulfate (triisopropanol ammonium $C_{12}$-fatty alcohol ether sulfate, CAS no. 89952-33-0) | 6.0 | 6.0 | 6.0 | — |
| Sunflower seed oil PEG-8 ester | 6.0 | 6.0 | — | 6.0 |
| Betaine | 2.5 | 2.5 | — | — |
| Quaternium-96 | 0.5 | 0.5 | 0.5 | 0.5 |
| [3-(behenoyloxy)-2-hydroxypropyl] trimethylammonium chloride (Quartamin BTC-131, CAS no. 69537-38-8) | to 100 | to 100 | — | — |
| 1,3-propanediol | — | — | to 100 | to 100 |

The preparations of examples 5 to 8 were packed in a single-chamber receptacle (pouch) made of a water-soluble foil from the company Monosol, type LX 20633 (Monosol, type SCP 20633: water-soluble foil, comprising polyvinyl alcohol/polyvinyl acetate copolymer, degree of hydrolysis approx. 89%, average molar mass=95,000 g/mol)

Each single chamber pouch was mixed lukewarm water and massaged by hand. This caused the foil to disintegrate and the shampoo formulation was released. This shampoo formulation was applied to wet hair, left to take effect for 1 minute, and then rinsed out with tap water. The hair was then dried. The hair was easy to comb and exhibited a soft hold.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic product for cleaning and care of keratinous fibers, comprising:
   (i) a pouch, comprising a sealed chamber, wherein the sealed chamber has a wall made from a water-soluble foil, and wherein the water-soluble foil comprises a polymer made from at least the monomer polyvinyl alcohol; and
   (ii) a shampoo composition, which is present inside the sealed chamber of the pouch, wherein the shampoo consists of, relative to its total weight, about 20% of capric acid/caprylic acid triglyceride, about 3% stearic acid, about 10% water, about 1% citric acid, about 12% triisopropanol ammonium $C_{12}$-fatty alcohol ether sulfate, about 6% sunflower seed oil polyethylene glycol-8 ester, about 6% betaine, about 2.5% quaternium-96, about 0.5% [3- (behenoyloxy)-2-hydroxyproyl] trimethylammonium chloride, and about 39% propanediol.

2. A cosmetic product for cleaning and care of keratinous fibers, comprising:
   (i) a pouch, comprising a sealed chamber, wherein the sealed chamber has a wall made from a water-soluble foil, and wherein the water-soluble foil comprises a polymer made from at least the monomer polyvinyl alcohol; and
   (ii) a shampoo composition, which is present inside the sealed chamber of the pouch, wherein the shampoo consists of, relative to its total weight, about 3% stearic acid, about 15% water, about 1% citric acid, about 39% glycerol, about 12% sodium- $C_{14}$-$C_{16}$-olefin-sulfonate, about 6% sunflower seed oil polyethylene glycol-8 ester, about 0.5% [3-(behenoyloxy)-2-hydroxyproyl] trimethylammonium chloride, and about 23.5% propanediol.

3. A cosmetic product for cleaning and care of keratinous fibers, comprising:
   (i) a pouch, comprising a sealed chamber, wherein the sealed chamber has a wall made from a water-soluble foil, and wherein the water-soluble foil comprises a polymer made from at least the monomer polyvinyl alcohol; and
   (ii) a shampoo composition, which is present inside the sealed chamber of the pouch, wherein the shampoo consists of, relative to its total weight, about 20% of capric acid/caprylic acid triglyceride, about 8% stearic acid, about 1% water, about 14% glycerol, about 6% sodium-$C_{14}$-$C_{16}$-olefin- sulfonate, about 6% triisopropanol ammonium $C_{12}$-fatty alcohol ether sulfate, about 6% sunflower seed oil polyethylene glycol-8 ester, about 2.5% betaine, about 0.5% quaternium-96, and about 36% [3- (behenoyloxy)-2-hydroxyproyl] trimethylammonium chloride.

4. A method for cleaning and caring for the hair, wherein a cosmetic product according to one of claim 1, 2 or 3 is mixed with water, applied to the hair and after an exposure period of from about 10 seconds to about 10 minutes is rinsed out again.

* * * * *